(12) United States Patent
Xu et al.

(10) Patent No.: US 8,492,127 B2
(45) Date of Patent: Jul. 23, 2013

(54) BACILLUS COAGULANS STRAINS AND THEIR APPLICATIONS IN L-LACTIC ACID PRODUCTION

(75) Inventors: Ping Xu, Shanghai (CN); Limin Wang, Shanghai (CN); Bo Zhao, Shanghai (CN); Cuiqing Ma, Shanghai (CN); Fei Su, Shanghai (CN); Fei Tao, Shanghai (CN); Hongzhi Tang, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 0 days.

(21) Appl. No.: 13/698,708

(22) PCT Filed: Nov. 22, 2010

(86) PCT No.: PCT/CN2010/001871
§ 371 (c)(1),
(2), (4) Date: Nov. 19, 2012

(87) PCT Pub. No.: WO2011/143800
PCT Pub. Date: Nov. 24, 2011

(65) Prior Publication Data
US 2013/0143286 A1 Jun. 6, 2013

(30) Foreign Application Priority Data
May 20, 2010 (CN) .......................... 2010 1 0176868

(51) Int. Cl.
*C12P 7/56* (2006.01)
(52) U.S. Cl.
USPC .......................... 435/139; 435/160; 435/252.3
(58) Field of Classification Search
None
See application file for complete search history.

(56) References Cited

U.S. PATENT DOCUMENTS
5,079,164 A  1/1992  Kirkovits et al.
2005/0250192 A1  11/2005  Shanmugam et al.

FOREIGN PATENT DOCUMENTS
| CN | 1498265 A | 5/2004 |
|---|---|---|
| CN | 1906290 A | 1/2007 |
| CN | 101173242 A | 5/2008 |
| CN | 101285047 A | 10/2008 |
| CN | 101544993 A | 9/2009 |
| EP | 0 346 983 A2 | 12/1989 |
| JP | 58040093 A | 3/1983 |
| JP | 3027291 A | 2/1991 |
| WO | WO 02/074934 A1 | 9/2002 |
| WO | WO 2005/071061 A1 | 8/2005 |
| WO | WO 2005/086670 A2 | 9/2005 |

OTHER PUBLICATIONS

Altschul, Stephen F.; Gish, Warren; Miller, Webb; Myers, Eugene W.; and Lipman, David J., "Basic Local Alignment Search Tool," National Center for Biotechnology Information, National Library of Medicine, National Institutes of Health, J. Mol. Biol. (1990) 215, 403-410, © 1990 Academic Press Limited, accepted May 15, 1990.

Maas, Ronald H. W.; Bakker, Robert R.; Jansen, Mickel L. A.; Visser, Diana; de Jong, Ed; Eggink, Gerrit; and Weusthuis, Ruud A., "Lactic Acid Production from Lime-Treated Wheat Straw by *Bacillus coagulans*: Neutralization of Acid by Fed-Batch Addition of Alkaline Substrate," *Biotechnological Products and Process Engineering*, Appl Microbiol Biotechnol (2008) 78:751-758, © The Author(s) 2008, Revised Jan. 10, 2008/Accepted Jan. 10, 2008/Published online Feb. 5, 2008.

Michelson, Tiina; Kask, Karin; Jõgi, Eerik; Talpsep, Ene; Suitso, Indrek; and Nurk, Allan, "L(+)-Lactic Acid Producer *Bacillus coagulans* SIM-7 DSM 14043 and Its Comparison with *Lactobacillus delbrueckii* ssp. *lactis* DSM 20073," *Science Direct: Enzyme and Microbial Technology* 39 (2006) 861-867, Available online at www.sciencedirect.com, © 2006 Elsevier Inc., Revised Form Jan. 7, 2006, and Accepted Jan. 12, 2006.

Patel, Milind A.; Ou, Mark S.; Harbrucker, Roberta; Aldrich, Henry C.; Buszko, Marian L.; Ingram, Lonnie O.; and Shanmugam, K. T., "Isolation and Characterization of Acid-Tolerant, Thermophilic Bacteria for Effective Fermentation of Biomass-Derived Sugars to Lactic Acid," *Applied and Environmental Microbiology*, Journals.ASM.org, Downloaded from http://aem.asm.org/ on Jan. 25, 2013 by guest, Updated information and services can be found at http://aem.asm.org/content/72/5/3228.

PCT International Preliminary Report on Patentability issued in International Application No. PCT/CN2010/001871 dated Nov. 20, 2012.

PCT International Search Report issued in International Application No. PCT/CN2010/001871 dated Feb. 24, 2011.

PCT Written Opinion of the International Searching Authority issued in International Application No. PCT/CN2010/001871 dated Feb. 24, 2011.

Wang, Yan-bo, "Isolation, Identification and G Row th Characters of *Bascillus coagulans* Isolated from the Ponds," *J. Hydroecology*, 2(1):91-94 (2009), © 1994-2013 China Academic Journal Electronic Publishing House, http://www.cnki.net, Abstract p. 94.

*Primary Examiner* — Tekchand Saidha
(74) *Attorney, Agent, or Firm* — Finnegan, Henderson, Farabow, Garrett & Dunner, LLP (57) ABSTRACT

The invention is concerned with the strains of *B. coagulans* for lactic acid production and the related methods, in which the carbon sources are pentose or hexose or the agricultural or industrial wastes containing pentose or hexose or a mixture of both. According to the invention, the highest amount of L-lactic acid produced from glucose is 173 g/L, the optical purity is over 99%, the yield is up to 0.98, and the productivity is up to 2.4 g/L per hour. The highest amount of L-lactic acid produced from xylose is 195 g/L, the optical purity is over 99%, the yield is up to 0.98, and the productivity is up to 2.7 g/L per hour. The highest amount of L-lactic acid produced from reducing sugars in xylitol byproducts is 106 g/L, the optical purity is over 99%, and the productivity is up to 2.08 g/L per hour. The *B. coagulans* strains XZL4 (DSM No. 23183) and XZL9 (DSM No. 23184) of the invention can directly utilize various reducing sugars in xylitol byproducts to produce high amounts of L-lactic acid, which improves the production efficiency at low costs, and the strains are, thus, appropriate for industrial productions.

13 Claims, 1 Drawing Sheet

BACILLUS COAGULANS STRAINS AND THEIR APPLICATIONS IN L-LACTIC ACID PRODUCTION

CROSS REFERENCE TO RELATED APPLICATIONS

This application is a national stage application of International Application No. PCT/CN2010/001871, filed Nov. 22, 2010, which claims priority to Chinese Patent Application No. 201010176868.9, filed May 20, 2010, the entirety of both of which are incorporated herein by reference.

FIELD OF THE INVENTION

The invention is concerned with bacterial strains for the production of lactic acid and the related methods. To be more precise, it involves strains of *Bacillus coagulans* and a method for the production of high amounts of L-lactic acid using pentose or hexose.

BACKGROUND OF THE INVENTION

As an important organic acid, lactic acid is widely applied in food, chemistry, and pharmaceutical industries. The most important and extensive application of lactic acid is as a monomer for the synthesis of poly(lactic acid), which has good biocompatibility and biodegradability, and is considered as the most promising renewable material of the 21th century. Lactic acid is a chiral molecule, and its optical activity is bringing by a chiral center in the molecule. According to the optical rotation, lactic acid products can be separated into three classes, L-lactic acid, D-lactic acid, and racemic lactic acid. Owing to an extensive application of poly(L-lactic acid), the production of optically pure L-lactic acid had gained general attention from the beginning.

There are three major methods to produce lactic acid: chemical synthesis, enzymatic method, and biotechnological production. Compared to chemical and enzymatic methods, microbial fermentation has significant advantages, i.e., lactic acid can be produced from decomposition products such as glucose from starch and cellulose, which are renewable resources. In addition, an optically pure product of L-lactic acid or D-lactic acid or their mixtures in different proportions can be obtained through different fermentation methods with various strains. Because of the low cost and high safety, microbial fermentation is the major method for lactic acid production in large scale. According to the Chinese patent 200480036931.1, *Lactobacillus, Streptococcus, Enterococcus, Rhizopus*, etc., have the ability to produce lactic acid. Thermophilic *B. coagulans* is a new kind of strain that can be used for L-lactic acid production. In recent years, studies on the production of lactic acid by *Bacillus* have increased gradually due to the advantages of *Bacillus* strains, e.g., low nutrition requirement and high fermentation temperature that allows open fermentation associated with sharply lowered bacterial pollution during production courses and enhances the optical purity of L-lactic acid. Lactic acid produced with *Bacillus* strains were reported in the Japanese patents JP5840093, JP606200, and JP327291, the U.S. Pat. No. 5,079,164, and the Chinese patent 200810098908.5.

According to a search through previous literature, L-lactic acid production using *B. coagulans* from glucose were reported in the Chinese patents 200710176060.9, 200910028930.7, and 02806664.2. However, of all those *B. coagulans* strains, the ability of producing high amounts of lactic acid from pentoses such as xylose has not been shown. Especially in the patent "A method for L-lactic acid production and its exclusive strain of *B. coagulans*," the *B. coagulans* strain that has been used cannot utilize xylose according to the description.

A further search revealed that there are several *B. coagulans* strains that can produce L-lactic acid from glucose and xylose (US patent US 2005/0250192 A1). Among those separated strains, *Bacillus* sp. 36D1 possesses the strongest ability of utilizing hexose and pentose. However, low amounts of L-lactic acid could be produced by *Bacillus* sp. 36D1. For example, about 25.2 g/L L-lactic acid was produced by *Bacillus* sp. 36D1 from glucose and about 23.4 g/L L-lactic acid was produced by *Bacillus* sp. 36D1 from xylose. The highest amount of L-lactic acid was 55.5 g/L produced from reducing sugars (mainly pentose-xylose, hexose-glucose) in sugar cane bagasse with a long fermentation time (over 190 hours).

Currently, the main raw materials for industrial production of lactic acid are glucose, maize, rice, etc., that contain high levels of starch. The main problem using these materials is the high costs. Lactic acid fermentation using organic wastes containing carbohydrates could not only lower the production costs, but also solve the problems of waste resourcization. As a part of the worldwide attempts of protecting the environment and reducing the energy demand, the development of techniques that efficiently recycle organic wastes is underway here and abroad. Organic wastes contain pentoses (xylose, arabinose, etc.) and hexoses (glucose, etc.). However, most of the lactic acid-producing strains cannot use pentoses, which limits the application of organic wastes in lactic acid production. In China, parts of the commercially available xylitol are made from xylose, which is extracted from corncob hydrolyzate. In addition, during that process, many byproducts containing 50%-70% carbohydrates are generated, which will result in high amounts of waste and pollution if not recycled.

SUMMARY OF THE INVENTION

Aiming at removing the limitations of previous technologies, the present invention provides a method for producing high amounts of L-lactic acid using the related *B. coagulans* strains that can directly utilize all kinds of reducing sugars from xylitol byproducts, improves the production efficiency at low cost, and is appropriate for application in industrial productions.

The present invention bases on the following technological processes:

The present invention concerns the L-lactic acid producing strains of *B. coagulans* XZL4 (DSM No. 23183 deposited on 4 Dec. 2009 in Deutsche Sammlung für Mikroorganismen und Zellkulturen GmbH under the provisions of the Budapest Treaty) and XZL9 (DSM No. 23184 deposited on 4 Dec. 2009 in Deutsche Sammlung für Mikroorganismen und Zellkulturen GmbH under the provisions of the Budapest Treaty).

*B. coagulans* XZL4 DSM No. 23183 is a gram-positive microorganism. The nucleotide sequence of its 16S rRNA gene is shown in Seq. ID No. 1. It is a rod-shaped, endospore-forming bacterium, 0.8-0.9 μm in width and 3.0-5.0 μm in length. When grown on plates containing xylose, yeast extract, and peptone, colonies of the strain are round, milk-white, with a smooth surface and regular edge. The strain was isolated from soil samples near a corncob factory in Shandong province of China.

*B. coagulans* XZL9 DSM No. 23184 is a gram-positive microorganism. The nucleotide sequence of its 16S rRNA gene is shown in Seq. ID No. 2. It is a rod-shaped, endospore-forming bacterium, 0.8-0.9 μm in width and 3.0-5.0 μm in length. When grown on plates containing xylose, yeast extract, and peptone, colonies of the strain are small, round, light milk-white, with a smooth surface and regular edge. The strain was isolated from soil samples near a corncob factory in Shandong province of China.

According to the invention, the applications for producing L-lactic acid by using *B. coagulans* are as follows: at first, strains of *B. coagulans* are cultivated to obtain seed cultures, and fermentations are carried out to obtain L-lactic acid using agricultural or industrial wastes that contain pentose or hexose as carbon source in fermentation media.

Fermentations of the invention are carried out with a 10% (v/v) inoculum, at a temperature of 50-60° C. (the optimum temperature ranging from 50-55° C.) for 48-72 hours.

According to the invention, fed-batch fermentations are carried out, in which carbon sources need to be added if the amount of reducing sugar decreases to 20-30 g/L, to maintain reducing sugar concentrations at 30-70 g/L, or 50-70 g/L.

In the present invention, the fermentation media contain 40-200 carbon sources, 5-12 g/L nitrogen sources, 50-100 g/L neutralization agents, and water.

According to the invention, the fermentation pH ranges from 5.5 to 6.2.

According to the invention, carbon sources are pentose or hexose, or raw materials rich in pentose or hexose, or one of the following three carbohydrates:

(1) 40-150 g/L glucose;
(2) 40-100 g/L xylose;
(3) 100-200 g/L xylitol byproducts According to the invention, xylitol byproducts are commercially available from Shandong Longlive Bio-Technology Co., Ltd (China)., Shandong Futaste Pharmaceutical Co., Ltd (China)., and Shandong Xingtai Bio-Technology Co., Ltd (China). It is notable that the total sugar content varies with different batches and different companies. Byproducts of xylitol in the invention contain 50-70% carbohydrates, including 5%-10% (w/v) glucose, 40%-50% (w/v) xylose, and 10%-25% (w/v) arabinose.

According to the invention, the nitrogen source is a yeast extract used at a concentration of 5-12 g/L;

According to the invention, the neutralization agent is $CaCO_3$ used at a concentration of 50-100 g/L.

According to the invention, seed cultures of *B. coagulans* are obtained by cultivating *B. coagulans* XZL4 DSM No. 23183 or *B. coagulans* XZL9 DSM No. 23184 on slants and seed culture successively.

According to the invention, slant cultures are obtained as follows: *B. coagulans* XZL4 DSM No. 23183 or *B. coagulans* XZL9 DSM No. 23184 is inoculated on slant medium containing 15 g/L agar at a temperature of 45-55° C. for 24-48 hours.

According to the invention, seed cultures were obtained as follows: *B. coagulans* from slant medium is inoculated aseptically into 30 mL seed media at a temperature of 45-55° C. and cultivated statically. A neutralization agent is added to control the pH.

According to the invention, seed media contain: 40-60 g/L glucose, 5-10 g/L yeast extract. 20-40 g/L $CaCO_3$, and water. The optimum medium for seed cultures contains 50 g/L glucose, 10 g/L yeast extract, 20 g/L $CaCO_3$, and water, with a pH of 6.5.

According to the invention, the main carbon sources are glucose, xylose, and xylitol byproducts. The strains can directly utilize pentose and hexose to produce L-lactic acid, avoiding the separate process of metabolizing pentose. Using a proper fermentation process not only makes L-lactic acid production from raw materials easy at lower cost, but also helps to achieve a high level of lactic acid production ability.

The *B. coagulans* strains XZL4 DSM No. 23183 and XZL9 DSM No. 23184 in the invention can produce lactic acid from glucose or xylose at high levels. The amount of L-lactic acid produced from glucose can be as high as 173 g/L, with high optical purity (over 99%), high yield (98%), and high productivity (2.7 g/L per hour). The amount of L-lactic acid produced from xylitol byproducts can be as high as 106 g/L, with high optical purity (over 99%) and high productivity (2.08 g/L per hour). The strains used in the invention remain high production activities after many cycles of fermentation, instead of requiring regeneration. The strains can directly utilize glucose, xylose, and all kinds of reducing sugars from xylitol byproducts to produce high amounts of L-lactic acid. Thus, methods for L-lactic acid production according to this invention can improve production efficiency at low costs, and are appropriate for popularizing in industrial productions.

Figure 1:
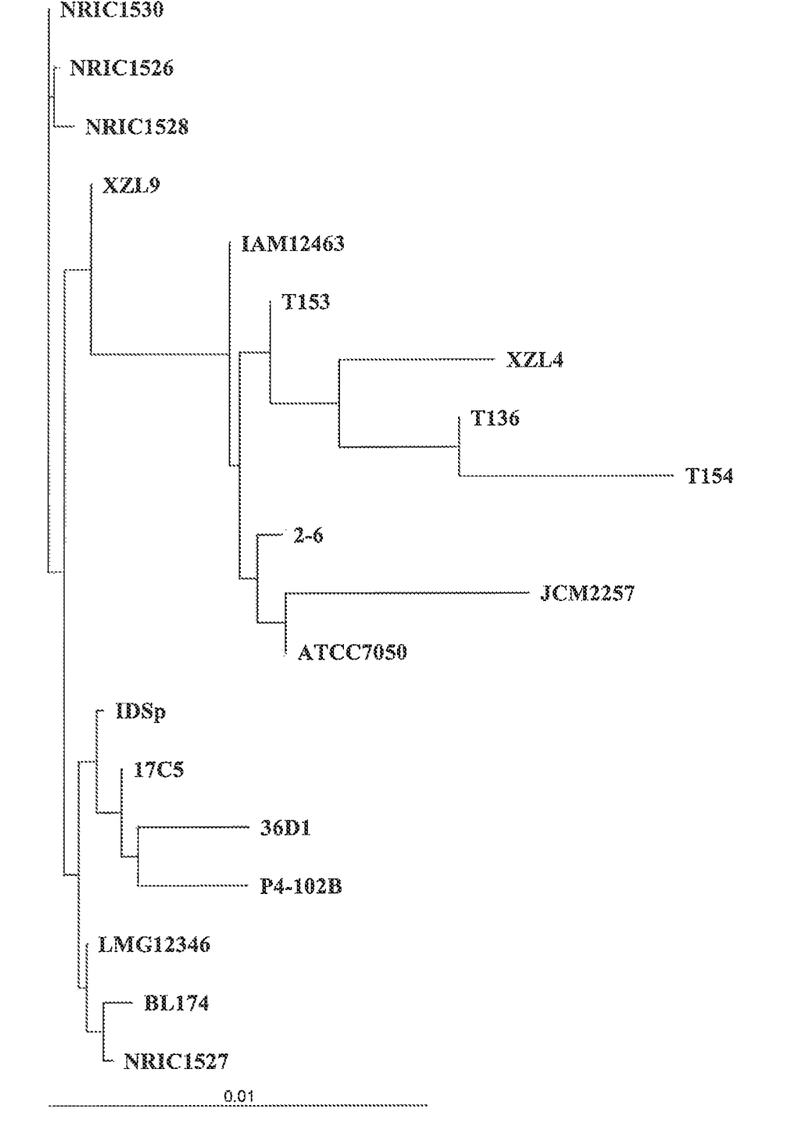
FIG. 1 shows the phylogenetic analysis of the sequences of 16S rRNA genes from *B. coagulans* XZL4 DSM No. 23183 and *B. coagulans* XZL9 DSM No. 23184.

In FIG. 1, horizontal distances in solid lines (sum of the lengths) stand for the evolution distances of strains, and the 11 strains of *B. coagulans* chosen as control have a close relationship with the strains used in the invention. *B. coagulans* 2-6 are from a Chinese patent strain (CN 200710176060.9), and the sequence of its 16S rRNA gene (SEQ ID NO: 3) was obtained by sequencing. *B. coagulans* 36D1 is a US patent strain (Pub. No: US 205/0250192 A1), and the sequence of its 16S rRNA gene (SEQ ID NO: 4) was obtained from the reference "Patel, M. A.; Ou, M. S.; Harbrucker, R.; Aldrich, H. C.; Buszko, M. L.; Ingram, L. O.; Shanmugam, K. T. Isolation and characterization of acid-tolerant, thermophilic bacteria for effective fermentation of biomass-derived sugars to lactic acid. *Appl. Environ. Microbiol.* 2006, 72, 3228-3235."

DETAILED DESCRIPTION OF THE INVENTION

Detailed descriptions for the application of the invention are provided in the following section. Based on the technological processes of the inventions, the descriptions offer detailed modes of execution and concrete procedures. To be noticed, the patent protection scope is not limited to the following embodiments.

Isolation, screening, and identification of *B. coagulans* XZL4 (DSM No. 23183) and *B. coagulans* XZL9 (DSM No. 23184) have been performed as follows:

1. Isolation and Screening

The media were prepared as follows:

Nutrient liquid medium: xylose 10 g/L, yeast extract 10 g/L, pH 6

Nutrient agar medium: xylose 10 g/L, yeast extract 10 g/L, $CaCO_3$ 20 g/L, agar 20 g/L, pH 6

Strains screening medium: xylose 10 g/L, Yeast extract 20 g/L, $CaCO_3$ 75 g/L, pH 6

The concrete operation process was carried out as follows:

First, 2 g of the soil samples collected near a corncob factory in Shandong was added to 50 mL of nutrient liquid medium, incubated at 50° C. for 6-10 hours, diluted, spread on the plates containing nutrient agar medium, and incubated for 24 hours. When colonies appeared, big colonies with large transparent circle were separately inoculated into fermentation medium, followed by statically incubation at 50° C. for 48 hours, and determination of the L-lactic acid concentration. After several rounds of isolation, two strains that produced higher amounts of L-lactic acid were obtained.

The above strains were subcultured repeatedly, and 10 rounds of fermentation were performed. The L-lactic acid production and yield of the 10th round of fermentation remained at the original level, which proved that these strains are indeed the desired strains, named XZL 4 and XZL 9.

2. Identification of the Strains

Observation of the morphologic characteristics and physiological and biochemical analysis were carried out at Deutsche Sammlung für Mikroorganismen und Zellkulturen GmbH (DSMZ). The molecular identification (16S rRNA gene sequences comparison) was carried out use the method described in the reference "Altschul, S. F.; Gish, W.; Miller, W.; Myers, E. W.; Lipman, D. J. Basic local alignment search tool. *J. Mol. Biol*, 1990, 215, 403-410." The results are as follows:

According to the protocol, two strains that can produce L-lactic acid from xylose were isolated.

The two strains presented are gram-positive, rod-shaped, endospore-forming microorganisms, 0.8-0.9 µm in width and 3.0-5.0 µm in length. Colonies of the strain XZL 4 appeared on the ager plates as round and milk-white colonies, with smooth surface and regular edge. Colonies of the strain XZL9 appeared on the agar plates as small, round, light milk-white colonies with regular edge. The detailed physiological and biochemical characteristics are summarized in Table 1 and Table 2.

TABLE 1

Physiological and biochemical characteristics of XZL4

| Test index | XZL4 | XZL9 |
|---|---|---|
| Anaerobic growth | + | + |
| Growth at 60° C. | + | + |
| Growth at 65° C. | − | − |
| V.P. | + | + |
| pH in V.P. | 4.6 | 4.5 |
| Fermentation of glucose, xylose, arabinose and fructose | + | + |
| Fermentation of mannitol | − | − |
| Gas from glucose | − | − |
| Metabolism of citric acid and propionic acid | − | − |
| Degradation of tyrosine | − | − |
| Phenylalanine deaminase | − | − |
| Lecithinase | − | − |
| Arginindihydrolase | − | − |
| Reduction of nitrate | + | − |
| Indole formation | − | − |
| Gelatin liquefaction | − | − |
| Hydrolysis of casein | + | w |
| Hydrolysis of starch and aesculin | + | + |
| Hydrolysis of Tween 80 | − | − |
| L-lactic acid homofermentation | + | + |

+, positive;
−, negative;
w, weak growth;
V.P., Voges-Proskauer

According to the retrieval through the TSBA40 4.10 Library, the fatty acid composition of XZL4 has high similarity (0.12) to *B. coagulans*. The 16S rRNA gene sequence of the strain (SEQ ID NO: 1) is different from 16S rRNA gene sequences that were reported or submitted to public databases, and has the highest homology with *B. coagulans* (99%), which suggests that XZL4 is a new strain. On the basis of the above characteristics and the analysis of its 16S rRNA gene diagnostic band, the L-lactic acid fermentation strain was identified as *B. coagulans* XZL4 (DSM No. 23183), and was deposited at Deutsche Sammlung für Mikroorganismen und Zellkulturen GmbH (DSMZ).

TABLE 2

Physiological and biochemical characteristics of XZL9

| Test index | XZL4 | XZL9 |
|---|---|---|
| Anaerobic growth | + | + |
| Growth at 60° C. | + | + |
| Growth at 65° C. | − | − |
| V.P. | + | + |
| pH in V.P. | 4.6 | 4.5 |
| Fermentation of glucose, xylose, arabinose, and fructose | + | + |
| Fermentation of mannitol | − | − |
| Gas from glucose | − | − |
| Metabolism of citric acid and propionic acid | − | − |
| Degradation of tyrosine | − | − |
| Phenylalanine deaminase | − | − |
| Lecithinase | − | − |
| Arginindihydrolase | − | − |
| Reduction of nitrate | + | − |
| Indole formation | − | − |
| Gelatin liquefaction | − | − |
| Hydrolysis of casein | + | w |
| Hydrolysis of starch and aesculin | + | + |
| Hydrolysis of Tween 80 | − | − |
| L-lactic acid homofermentation | + | + |

+, positive;
−, negative;
w, weak growth;
V.P., Voges-Proskauer

According to the retrieval through the TSBA40 4.10 Library, the fatty acid composition of XZL9 has high similarity (0.69) to *B. coagulans*. The 16S rRNA gene sequence of the strain (SEQ ID NO: 2) is different from 16S rRNA gene sequences that were reported or submitted to public databases, and has the highest homology with *B. coagulans* NRIC 1526 (99%), which suggests that XZL9 is a new strain. On the basis of the above characteristics and the analysis of its 16S rRNA gene diagnostic band, the L-lactic acid fermentation strain was identified as *B. coagulans* XZL9 (DSM No. 23184), and was deposited at Deutsche Sammlung für Mikroorganismen und Zellkulturen GmbH (DSMZ).

Further comparisons and analysis of 16S rRNA gene sequences and the differences on the evolutionary status of *B. coagulans* XZL4, XZL9, 2-6, and 36D1 are shown as FIG. 1. With regard to the evolutionary status, 2-6, XZL4, XZL9, and the standard strain ATCC7050 can be classified in one branch, but 36D1 is located in another branch, which probably indicates that 36D1 evolved from a different ancestor as compared to strains 2-6, XZL4, and XZL9. There are base differences between the 16S rRNA gene sequences of *B. coagulans* XZL9 and 36D1, located at the genetic sites 830, 890, 1262, 1267, 1268, 1286, 1308, 1315, 1344, 1345, and 1362. Differences between XZL9 and 2-6 were noted at the genetic sites 340, 1212, 1225, 1276, 1309, 1345, and 1346 (the genetic sites are based on the sequence of XZL9). Base differences between the 16S rRNA gene sequences of *B. coagulans* XZL4 and 36D1 were observed at the genetic sites 340, 830, 890, 1214, 1225, 1264, 1268, 1269, 1275, 1316, 1345, and 1346. Base differences between XZL4 and 2-6 were found at the genetic site 3 (the genetic sites are based on the sequence of XZL4). Base differences between XZL4 and XZL9 were noted at the genetic sites 1, 340, 1212, 1224, 1274, 1374, and 1375 (the genetic sites are based on the sequence of XZL9).

The involved strains of *B. coagulans*, XZL4 (DSM No. 23183) and XZL9 (DSM No. 23184), were isolated from soil samples near a corncob factory in Shandong.

Procedures of L-lactic acid fermentation using *B. coagulans* XZL4 (DSM No. 23183) and XZL9 (DSM No. 23184) were as follows:

(1) Slant culture: Strains of *B. coagulans* XZL4 (DSM No. 23183) and XZL9 (DSM No. 23184) were inoculated into slants containing 15 g/L agar and incubated at 50-60° C. for 24-48 hours.

(2) Seed culture: Slant cultures from (1) were inoculated in 30 mL seed medium and incubated at 50-60° C. for 10-24 hours to obtain seed cultures. A neutralizing agent was added to keep the pH value of cultures constant.

(3) Fermentation: Seed cultures were inoculated into fermentation medium with an inoculum of 10% (v/v), and cultivated at 50-60° C. for 48-72 hours.

The optimal temperature for cultures in procedures (1), (2), and (3) ranged between 50-55° C.

The neutralizing agent used in procedures (2) and (3) was $CaCO_3$.

During the above fermentation courses, samples were taken every three hours, heated to 80-100° C., centrifuged at 6,000 rpm for 5 minutes to obtain supernatants, and applied for determination of the concentrations of L-lactic acid, D-lactic acid, glucose, and xylose, followed by calculating the yield, L-lactic acid productivity, and optical purity of L-lactic acid.

The DNS method was used to determine the total amount of reducing sugars. To determine the glucose concentration, fermentation cultures were diluted, centrifuged, and the glucose concentration was measured by using the Biosensor Analyzer SBA-40C (Shandong Academy of Sciences). The Biosensor Analyzer SBA-40C has sensors of immobilized enzymes, by which glucose oxygen and water are catalyzed to form hydrogen peroxide. Hydrogen peroxide contacts with a platinum-silver electrode and generates electronic signals, which are linearly proportional to the concentrations of glucose. Therefore, glucose concentrations can be obtained by measuring current signal intensities.

A xylose kit (Nanjing Jiancheng Biochemistry Co., Ltd, China) was used to measure the amount of xylose.

The method for measuring the productions of L-lactic acid and D-lactic acid (concentration or content of culture broth, g/L) is based on high performance liquid chromatography (HPLC) using the Agilent 1100 equipped with chiral column (Mitsubishi Chemical Holdings Corporation, MCI GEL-CRS10 W(3µ) 4.6 ID×50 mm, optical isomers separation). The specific operating condition was as follows: mobile phase 0.002 mol/L $CuSO_4$, flow rate 0.4 mL min$^{-1}$, injection volume 10 µL, tunable UV detector, detection wavelength 254 nm, temperature 25° C. Standard curves were generated by using standard L-lactic acid and D-lactic acid. The concentrations of L-lactic acid and D-lactic acid in the fermentation broth were calculated by referring to the standard curves.

In the present invention, standard D-lactic acid (L0625-25MG) and L-lactic acid (L1750-10G) were purchased from Sigma-Aldrich Corporation. According to the HPLC method, the retention time of D-lactic acid is 10.150 minutes.

Optical purity is defined as enantiomeric excess (ee) of one isomer over the other. In the present invention, the ee value is defined as $$\left(\frac{(L\text{-lactic acid}) - (D\text{-lactic acid})}{(L\text{-lactic acid}) + (D\text{-lactic acid})}\right) \times 100\%.$$

Yield (g/g) is defined as $\frac{L\text{-lactic acid production (g/L)}}{\text{substrate consumption (g/L)}} \times 100\%.$ Substrates contain glucose, xylose, or total sugars. Productivity (g/L per hour) is defined as $$\frac{L\text{-lactic acid production (g/L)}}{\text{fermentation time (h)}}.$$

EXAMPLE 1

Batch fermentation of L-lactic acid from glucose by using *B. coagulans* XZL4 DSM No. 23183 and XZL9 DSM No. 23184 in flasks:

The media compositions of the example are as follows:

Slant medium per liter contains: xylose 30 g, yeast extract 10 g, $CaCO_3$ 10 g, agar 15 g, and water. The pH value of the slant medium is 6.5. Sterilization is conducted at 115° C. for 20 minutes.

Seed medium per liter contains: glucose 50 g, yeast extract 10 g, $CaCO_3$ 20 g, and water. The pH value of the medium is 6.5. Sterilization is conducted at 115° C. for 20 minutes.

Fermentation media per liter contain: glucose 55-150 g, yeast extract 10 g, $CaCO_3$ 60 g, and water. The pH value of the medium is in the range 5.5-7. Sterilization is conducted at 115° C. for 20 minutes.

The method for L-lactic acid production in the invention includes the following procedures:

(1) Slant culture: *B. coagulans* XZL4 (DSM No, 23183) and XZL9 (DSM No. 23184) were inoculated into slant medium and incubated at 50° C. for 24 hours;

(2) Seed culture: Two loops of the strains from procedure (1) were inoculated aseptically into a 100-mL flask containing 30 mL seed medium and incubated at 50° C. for 20 hours to obtain seed cultures;

(3) Fermentation culture: 10 mL of seed cultures from procedure (2) was inoculated into a 300-mL flask containing 90 mL fermentation medium and statically fermented at 50° C. The fermentation process was stopped when the contents of L-lactic acid and glucose were steady.

After fermentation, the concentrations of L-lactic acid and glucose were measured, and L-lactic acid productivities were calculated according to the methods mentioned above.

The experiment was conducted in triplicate. The results are shown in Table 3.

TABLE 3

Results of l-lactic acid production from glucose

| | XZL4 | | | XZL9 | | |
|---|---|---|---|---|---|---|
| Glucose concentration (g/L) | L-lactic acid concentration (g/L) | Yield (g/g) | Productivity (g/L per h) | L-lactic acid concentration (g/L) | Yield (g/g) | Productivity (g/L per h) |
| 55 | 54 ± 1 | 0.98 | 1.2 | 52 ± 2 | 0.95 | 1.2 |
| 85 | 83 ± 0 | 0.98 | 2.3 | 81 ± 2 | 0.95 | 2.3 |
| 150 | 143 ± 1 | 0.95 | 2.0 | 132 ± 2 | 0.88 | 1.8 |

EXAMPLE 2

Batch fermentation of L-lactic acid from xylose by using *B. coagulans* XZL4 DSM No. 23183 and XZL9 DSM No. 23184 in flasks:

The media compositions of the example are as follows:

Slant medium and seed medium are the same as in example 1.

Fermentation medium per liter contains: xylose 55-100 g, yeast extract 10 g, $CaCO_3$ 60 g, and water. The pH value of the medium is in the range 5.5-7. Sterilization is conducted at 115° C. for 20 minutes.

The method for Lactic acid production in the invention includes the following procedures:

(1) Slant culture: as in example 1;
(2) Seed culture: as in example 1;
(3) Fermentation culture: as in example 1.

Fermentation was stopped when the contents of L-lactic acid and glucose were steady. L-lactic acid and glucose concentrations were measured, and L-lactic acid productivities were calculated according to the methods mentioned above.

The experiment was conducted in triplicate. The results are shown in Table 4.

TABLE 4

Results of l-lactic acid production from xylose

| | XZL4 | | | XZL9 | | |
|---|---|---|---|---|---|---|
| Xylose concentration (g/L) | L-lactic acid concentration (g/L) | Yield (g/g) | Productivity (g/L per h) | L-lactic acid concentration (g/L) | Yield (g/g) | Productivity (g/L per h) |
| 55 | 54 ± 1 | 0.98 | 1.1 | 53 ± 2 | 0.96 | 1.1 |
| 75 | 69 ± 3 | 0.92 | 1.4 | 55 ± 1 | 0.73 | 1.1 |
| 100 | 85 ± 2 | 0.85 | 1.8 | 63 ± 2 | 0.63 | 1.3 |

EXAMPLE 3

Batch fermentation of L-lactic acid from xylitol byproducts by using *B. coagulans* XZL4 DSM No. 23183 and XZL9 DSM No. 23184 in flasks:

The media compositions of the example are as follows:

Slant medium and seed medium are the same as in example 1.

Fermentation medium per liter contains: xylitol 75-150 g, yeast extract 10 g, $CaCO_3$ 60 g, and water. The pH value of the medium is in the range 5.5-7. Sterilization is conducted at 115° C. for 20 minutes.

The method for L-lactic acid production in the invention includes the following procedures:

(1) Slant culture: as in example 1;
(2) Seed culture: as in example 1;
(3) Fermentation culture: 10 mL of seed cultures from procedure (2) was inoculated into a 300-mL flask containing 90 mL fermentation medium and statically fermented at 50° C. for 48 hours.

After the fermentation was stopped, the amounts of L-lactic acid and total reducing sugar were measured, and L-lactic acid productivities were calculated according to the methods mentioned above.

The experiment was conducted in triplicate. The results are shown in Table 5.

TABLE 5

Results of l-lactic acid production from xylitol byproducts

| Xylitol byproductus concentration (g/L) | XZL4 | | | XZL9 | | |
|---|---|---|---|---|---|---|
| | L-lactic acid concentration (g/L) | Yield (g/g) | Productivity (g/L per h) | L-lactic acid concentration (g/L) | Yield (g/g) | Productivity (g/L per h) |
| 75 | 31 ± 1 | 0.41 | 0.7 | 33 ± 1 | 0.44 | 0.7 |
| 100 | 35 ± 2 | 0.35 | 0.7 | 42 ± 1 | 0.42 | 0.9 |
| 125 | 50 ± 2 | 0.40 | 1.0 | 45 ± 2 | 0.36 | 0.9 |
| 150 | 54 ± 3 | 0.36 | 1.1 | 45 ± 2 | 0.30 | 0.9 |

EXAMPLE 4

Batch fermentation of L-lactic acid from xylitol byproducts by *B. coagulans* XZL4 DSM No. 23183 and XZL9 DSM No. 23184 at 55° C. in flasks:

The media compositions of the example are as follows:

Slant medium and seed medium are the same as in example 1.

Fermentation medium per liter contains: xylitol byproducts 150 g, yeast extract 10 g, $CaCO_3$ 100 g, and water. The pH value of the medium is in the range 5.5-7. Sterilization is conducted at 115° C. for 20 minutes.

The method for L-lactic acid production in the invention includes the following procedures:

(1) Slant culture: as in example 1;
(2) Seed culture: as in example 1;
(3) Fermentation culture: 10 mL of seed cultures from procedure (2) was inoculated into a 300-mL flask containing 90 mL fermentation medium and statically fermented at 55° C. for 48 hours.

After the fermentation was stopped, the amounts of L-lactic acid and total reducing sugar were measured, and L-lactic acid productivities were calculated according to the methods mentioned above.

The experiment was conducted in triplicate. The results show that the amount of L-lactic acid produced by XZL4 DSM No. 23183 is 57±3 g/L and the L-lactic acid productivity is 1.19 g/L per hour. The amount of L-lactic acid produced by XZL9 DSM No. 23184 is 53±2 g/L and the L-lactic acid productivity is 1.10 g/L per hour.

EXAMPLE 5

Batch fermentation of L-lactic acid from xylitol byproducts by using a *B. coagulans* XZL4 DSM No. 23183 and XZL9 DSM No. 23184 at 60° C. in flasks:

The media compositions of the example are as follows:

Slant medium and seed medium are the same as in example 1.

Fermentation medium per liter contains: xylitol byproducts 200 g, yeast extract 5 g, $CaCO_3$ 100 g, and water. The pH value of the medium is in the range 5.5-7. Sterilization is conducted at 115° C. for 20 minutes.

The method for L-lactic acid production in the invention includes the following procedures:

(1) Slant culture: as in example 1;
(2) Seed culture: as in example 1;
(3) Fermentation culture: 10 mL of seed cultures from procedure (2) was inoculated into a 300-mL flask containing 90 mL fermentation medium and statically fermented at 60° C. for 48 hours.

After the fermentation was stopped, the amounts of L-lactic acid and total reducing sugar were measured, and L-lactic acid productivities were calculated according to the methods mentioned above.

The experiment was conducted in triplicate. The results show that the amount of L-lactic acid produced by XZL4 DSM No. 23183 is 48±6 g/L and L-lactic acid productivity is 1.0 g/L per hour. The amount of L-lactic acid produced by XZL9 DSM No. 23184 is 44±2 g/L and the L-lactic acid productivity is 0.92 g/L per hour.

EXAMPLE 6

Feed-batch fermentation of L-lactic acid from 100 g/L glucose by using *B. coagulans* XZL4 DSM No. 23183 and XZL9 DSM No. 23184 in a 50-L fermentor:

The media compositions of the example are as follows:

Slant medium and seed medium are the same as in example 1.

Fermentation medium per liter contains: glucose 100 g, yeast extract 12 g, $CaCO_3$ 100 g, and water. The pH value of the medium is in the range 5.5-7. Sterilization is conducted at 115° C. for 20 minutes.

The method for L-lactic acid production in the invention includes the following procedures:

(1) Slant culture: as in example 1;
(2) Seed culture: Two loops of the strains from procedure (1) were inoculated aseptically into a 100-mL flask containing 30 mL seed medium and incubated at 50° C. for 20 hours to obtain seed culture 1. Next, 30 mL seed culture 1 was inoculated into a 500-mL flask containing 300 mL seed culture and incubated at 50° C. for 20 hours to obtain seed culture 2. Further amplification of the seed culture was carried out in the same manner to obtain 4 L seed culture 3.

(3) Fermentation culture: 4 L of seed culture 3 from procedure (2) was inoculated into a 50-L fermentor (BIOTECH Shanghai Baoxing Bio-Engineering Equipment Co., Ltd) containing 36 L fermentation medium and statically fermented at 50° C. Samples were taken every three hours to measure the concentrations of residual sugar and L-lactic acid in the fermentation broth. When the concentration of glucose was reduced to 20-30 g/L, glucose was added to a final concentration of 50-70 g/L; in general, glucose was added twice. Fermentation was stopped when the consumption rate of glucose was steady.

After the fermentation was stopped, the concentrations of L-lactic acid and residual glucose were measured, and L-lactic acid productivities were calculated according to the methods mentioned above.

The experiment was conducted in triplicate. The amount of L-lactic acid produced by XZL4 DSM No. 23183 is 173±3 g/L, the fermentation time is 72 hours, the L-lactic acid productivity is 2.40 g/L per hour, the yield is 0.98, and the optical purity is 99.2%. The amount of L-lactic acid produced by XZL9 DSM No. 23184 is 171±5 g/L, the fermentation time is 72 hours, the L-lactic acid productivity is 2.38 g/L per hour, the yield is 0.96, and the optical purity is 99.3%.

EXAMPLE 7

Feed-batch fermentation of L-lactic acid from 100 g/L xylose by using a coagulans XZL4 DSM No. 23183 and XZL9 DSM No. 23184 in a 50-L fermentor:

The media compositions of the example are as follows:

Slant medium and seed medium are the same as in example 1.

Fermentation medium per liter contains: xylose 100 g, yeast extract 12 g, $CaCO_3$ 100 g, and water. The pH value of the medium is in the range 5.5-7. Sterilization is conducted at 115° C. for 20 minutes.

The method for L-lactic acid production in the invention includes the following procedures:

(1) Slant culture: as in example 1;
(2) Seed culture: as in example 6;
(3) Fermentation culture: 4 L of seed culture 3 from procedure (2) was inoculated into a 50-L fermentor (BIOTECH Shanghai Baoxing Bio-Engineering Equipment Co., Ltd) containing 36 L fermentation medium and statically fermented at 50° C. Samples were taken every 3 hours to measure the concentrations of residual sugar and L-lactic acid in the fermentation broth. When the concentration of xylose was reduced to 20-30 g/L, xylose was added to a final concentration of 50-70 g/L; in general, xylose was added twice. Fermentation was stopped when the consumption rate of xylose was steady.

After the fermentation was stopped, the concentrations of L-lactic acid and residual xylose were measured, and L-lactic acid productivities were calculated according to the methods mentioned above.

The experiment was conducted in triplicate. The amount of L-lactic acid produced by XZL4 DSM No. 23183 is 195±1 g/L, the L-lactic acid productivity is 2.70 g/L per hour, the yield is 0.98, and the optical purity is 99.3%. The amount of L-lactic acid produced by XZL9 DSM No. 23184 is 186±4 g/L, the fermentation time is 72 hours, the L-lactic acid productivity is 2.58 g/L per hour, the yield is 0.97, and the optical purity is 99.4%.

EXAMPLE 8

Feed-batch fermentation of L-lactic acid from 100 g/L xylitol byproducts by using *B. coagulans* XZL4 DSM No. 23183 and XZL9 DSM No. 23184 in a 50-L fermentor:

The media compositions of the example are as follows:
Slant medium and seed medium are the same as in example 1.

Fermentation medium per liter contains: xylitol byproducts 100 g, yeast extract 12 g. $CaCO_3$ 100 g, NaCl 0.1 g, $K_2HPO_4$ 0.5 g, $MgSO_4$ 0.2 g, and water for the rest. The pH value of the medium is in the range 5.5-7. Sterilization is conducted at 115° C. for 20 minutes.

The method for L-lactic acid production in the invention includes the following procedures:
(1) Slant culture: as in example 1;
(2) Seed culture: as in example 6.
(3) Fermentation culture: 4 L of seed culture 3 from procedure (2) was inoculated into a 50-L fermentor (BIOTECH Shanghai Baoxing Bio-Engineering Equipment Co., Ltd) containing 36 L fermentation medium and statically fermented at 50° C. Samples were taken every 3 hours to measure the concentrations of residual sugar and L-lactic acid in the fermentation broth. When the concentration of total sugar was reduced to 20-30 g/L, xylitol byproducts were added to a final concentration of 50-70 g/L; in general, xylitol byproducts were added twice. Fermentation was stopped when the consumption rate of total sugar was steady.

After the fermentation was stopped, the concentrations of L-lactic acid and residual total sugar were measured, and L-lactic acid productivities were calculated according to the methods mentioned above.

The experiment was conducted in triplicate. The amount of L-lactic acid produced by XZL4 DSM No. 23183 is 95±2 g/L, the L-lactic acid productivity is 1.98 g/L per hour, and the optical purity is 99.1%. The amount of L-lactic acid produced by XZL9 DSM No. 23184 is 92±5 g/L, the L-lactic acid productivity is 1.92 g/L per hour, and the optical purity is 99.3%.

EXAMPLE 9

Feed-batch fermentation of L-lactic acid from 200 g/L xylitol byproducts by using *B. coagulans* XZL4 DSM No. 23183 and XZL9 DSM No. 23184 in a 50-L fermentor:

The media compositions of the example are as follows:
Slant medium and seed medium are the same as in example 1.

Fermentation medium per liter contains: xylitol byproducts 200 g, yeast extract 12 g, $CaCO_3$ 100 g, NaCl 0.1 g, $K_2HPO_4$ 0.5 g, $MgSO_4$ 0.2 g, and water. The pH value of the medium is in the range 5.5-7. Sterilization is conducted at 115° C. for 20 minutes.

The method for L-lactic acid production in the invention includes the following procedures:
(1) Slant culture: as in example 1;
(2) Seed culture: as in example 6.
(3) Fermentation culture: as in example 8.

After the fermentation was stopped, the concentrations of L-lactic acid and residual total sugar were measured, and L-lactic acid productivities were calculated according to the methods mentioned above.

The experiment was conducted in triplicate. The fermentation time is 72 hours. The amount of L-lactic acid produced by XZL4 DSM No. 23183 is 98±5 g/L, the L-lactic acid productivity is 1.36 g/L per hour, and the optical purity is 99.2%. The amount of L-lactic acid produced by XZL9 DSM No. 23184 is 94±5 g/L, L-lactic acid productivity is 1.31 g/L per hour, optical purity is 99.1%.

EXAMPLE 10

Feed-batch fermentation of L-lactic acid from 150 g/L xylitol byproducts by using *B. coagulans* XZL4 DSM No. 23183 and XZL9 DSM No. 23184 in a 50-L fermentor:

The media compositions of the example are as follows:
Slant medium and seed medium are the same as in example 1.

Fermentation medium per liter contains: xylitol byproducts 150 g, yeast extract 12 g, $CaCO_3$ 100 g, NaCl 0.1 g, $K_2HPO_4$ 0.5 g, $MgSO_4$ 0.2 g, and water. The pH value of the medium is in the range 5.5-7. Sterilization is conducted at 115° C. for 20 minutes.

The method for L-lactic acid production in the invention includes the following procedures:
(1) Slant culture: as in example 1;
(2) Seed culture: as in example 6.
(3) Fermentation culture: as in example 8.

After the fermentation was stopped, the concentration of L-lactic acid and residual total sugar were measured, and L-lactic acid productivities were calculated according to the methods mentioned above.

The experiment was conducted in triplicate. The fermentation time is 51 hours. The amount of L-lactic acid produced by XZL4 DSM No. 23183 is 106±3 g/L, the L-lactic acid productivity is 2.08 g/L per hour, and the optical purity is 99.1%. The amount of L-lactic acid produced by XZL9 DSM No. 23184 is 100±6 g/L the L-lactic acid productivity is 1.96 g/L per hour, and the optical purity is 99.3%.

What is claimed is:

1. An isolated L-lactic acid producing strain of *Bacillus coagulans* chosen from:
   *Bacillus coagulans* XZL4 (DSM No. 23183), and
   *Bacillus coagulans* XZL9 (DSM No. 23184).

2. An L-lactic acid production method comprising:
   cultivating the *Bacillus coagulans* strain according to claim 1 to obtain a seed culture, and
   fermenting the seed culture in a fermentation medium.

3. The L-lactic acid production method according to claim 2, wherein the fermentation medium comprises carbon sources from agricultural or industrial wastes comprising pentose and/or hexose.

4. The L-lactic acid production method according to claim 2, wherein the fermentation process is performed with an inoculation amount of 10% (v/v) at 50-60° C. for 48-72 hours.

5. The L-lactic acid production method according to claim 2, wherein the fermentation process comprises a feed-batch technique in which carbon sources are added when the concentration of a reducing sugar is below 20-30 g/L, to maintain the total reducing sugar concentration at 30-70 g/L or 50-70 g/L.

6. The L-lactic acid production method according to claim 2, wherein the fermentation medium comprises carbon sources (40-200 g/L), nitrogen sources (5-12 g/L), a neutralizing agent (50-100 g/L), and water.

7. The L-lactic acid production method according to claim 2, wherein carbon sources in the fermentation medium comprise pentose and/or hexose, or are obtained from agricultural or industrial wastes comprising glucose and/or xylose.

8. The L-lactic acid production method according to claim 7, wherein the carbon sources comprise glucose (40-150 g/L), xylose (40-100 g/L), or xylitol byproducts (100-200 g/L).

9. The L-lactic acid production method according to claim 2, wherein the seed culture of *Bacillus coagulans* is obtained by using slant cultivation and subsequent seed cultivation of the *Bacillus coagulans* strain.

10. The L-lactic acid production method according to claim 9, wherein the slant cultivation comprises inoculating a slant medium comprising 15 g/L agar with the *Bacillus coagulans* strain and cultivating at 50-60° C. for 24-48 hours.

11. The L-lactic acid production method according to claim 9, wherein the subsequent seed cultivation comprises inoculating 30 mL of a seed culture medium with a slant culture of *Bacillus coagulans*, static incubation at 50-60° C. for 10-24 hours, and adding a neutralizing agent for controlling the pH to obtain the seed culture.

12. The L-lactic acid production method according to claim 11, wherein the seed culture medium comprises: glucose 40-60 g/L, yeast extract 5-10 g/L, $CaCO_3$ 20-40 g/L, and water, and the pH value of the medium is 6.5.

13. The L-lactic acid production method according to claim 12, wherein the seed culture medium comprises: glucose 50 g/L, yeast extract 10 g/L, $CaCO_3$ 20 g/L, and water.

* * * * *

SEQUENCE LISTING

<160> NUMBER OF SEQ ID NOS: 4

<210> SEQ ID NO 1
<211> LENGTH: 1466
<212> TYPE: DNA
<213> ORGANISM: Bacillus coagulans
<220> FEATURE:
<223> OTHER INFORMATION: B. coagulans XZL4 DSM No. 23183

```
<400> SEQUENCE: 1
ctctgccacc ttcggcggct ggctccgtaa aggttacctc accgacttcg ggtgttacaa      60
actctcgtgg tgtgacgggc ggtgtgtaca aggcccggga acgtattcac cgcggcatgc     120
tgatccgcga ttactagcga ttccggcttc atgcaggcgg gttgcagcct gcaatccgaa     180
ctgggaatgg ttttctggga ttggcttaac ctcgcggtct cgcagccctt tgtaccatcc     240
attgtagcac gtgtgtagcc caggtcataa ggggcatgat gatttgacgt catccccacc     300
ttcctccggt ttgtcaccgg cagtcacctt agagtgccca actcaatgct ggcaactaag     360
gtcaagggtt gcgctcgttg cgggacttaa cccaacatct cacgacacga gctgacgaca     420
accatgcacc acctgtcact ctgtcccccg aaggggaagg ccctgtctcc agggaggtca     480
gaggatgtca agacctggta aggttcttcg cgttgcttcg aattaaacca catgctccac     540
cgcttgtgcg gccccccgtc aattcctttg agtttcagcc ttgcggccgt actcccagg     600 cggagtgctt aatgcgttag ctgcagcact aaagggcgga accctctaa cacttagcac     660 tcatcgttta cggcgtggac taccagggta tctaatcctg tttgctcccc acgctttcgc     720
gcctcagcgt cagttacaga ccagagagcc gccttcgcca ctggtgttcc tccacatctc     780
tacgcatttc accgctacac gtggaattcc actctcctct tctgcactca agcctcccag     840
tttccaatga ccgcttgcgg ttgagccgca agatttcaca tcagacttaa gaagccgcct     900
gcgcgcgctt tacgcccaat aattccggac aacgcttgcc acctacgtat taccgcggct     960
gctggcacga gtagccgt ggcttttctgg ccgggtaccg tcaaggcgcc gccctgttcg    1020
aacggcactt gttcttcccc ggcaacagag ttttacgacc cgaaggcctt cttcactcac    1080
gcggcgttgc tccgtcagac tttcgtccat tgcggaagat tccctactgc tgcctcccgt    1140
aggagtttgg gccgtgtctc agtcccaatg tggccgatca ccctctcagg tcggctacgc    1200
atcgttgcct tggtgggccg ttaccccgcc aactagctaa tgcgccgcgg gcccatctgt    1260
aagtggcagc gaagccgcc tttccttttt cctccatgcg gaggaaaaaa ctatccggta    1320
ttagccccgg tttcccggcg ttatcccagt cttacaggca ggttgcccac gtgttactca    1380
cccgtccgcc gctaaccttt taaaagcaag cttttaaaag gtccgcacga cttgcagtat    1440
taggcacgcc gccaagcctt tggccc                                         1466

<210> SEQ ID NO 2
<211> LENGTH: 1458
<212> TYPE: DNA
<213> ORGANISM: Bacillus coagulans
<220> FEATURE:
<223> OTHER INFORMATION: B. coagulans XZL9 DSM No. 23184

<400> SEQUENCE: 2
gggagagctg gcggcgtgcc taatactgca agtcgtgcgg accttttaaa agcttgcttt      60
taaaaggtta gcggcggacg ggtgagtaac acgtgggcaa cctgcctgta agatcgggat     120
aacgccggga aaccggggct aataccggat agtttttcc tccgcatgga ggaaaaagga     180
aagacggctt cggctgccac ttacagatgg gcccgcggcg cattagctag ttggtgggt     240 aacggctcac caaggcaacg atgcgtagcc gacctgagag ggtgatcggc cacattggga     300
ctgagacacg gcccaaactc ctacgggagg cagcagtagg gaatcttccg caatggacga     360
aagtctgacg gagcaacgcc gcgtgagtga agaaggcctt cgggtcgtaa aactctgttg     420
ccggggaaga acaagtgccg ttcgaacagg gcggcgcctt gacggtaccc ggccagaaag     480
ccacggctaa ctacgtgcca gcagccgcgg taatacgtag gtggcaagcg ttgtccggaa     540
```

```
ttattgggcg taaagcgcgc gcaggcggct tcttaagtct gatgtgaaat cttgcggctc      600
aaccgcaagc ggtcattgga aactgggagg cttgagtgca gaagaggaga gtggaattcc      660
acgtgtagcg gtgaaatgcg tagagatgtg gaggaacacc agtggcgaag gcggctctct      720
ggtctgtaac tgacgctgag gcgcgaaagc gtggggagca acaggattag ataccctgg       780 tagtccacgc cgtaaacgat gagtgctaag tgttagaggg tttccgccct ttagtgctgc      840
agctaacgca ttaagcactc cgcctgggga gtacggccgc aaggctgaaa ctcaaaggaa      900
ttgacggggg cccgcacaag cggtggagca tgtggtttaa ttcgaagcaa cgcgaagaac      960
cttaccaggt cttgacatcc tctgacctcc ctggagacag gccttcccc ttcggggggac     1020 agagtgacag gtggtgcatg gttgtcgtca gctcgtgtcg tgagatgttg ggttaagtcc     1080
cgcaacgagc gcaacccttg accttagttg ccagcattca gttgggcact ctaaggtgac     1140
tgccggtgac aaaccggagg aaggtgggga tgacgtcaaa tcatcatgcc ccttatgacc     1200
tgggctacac acgtgctaca atggatggta caaagggctg cgagaccgcg aggttaagcc     1260
aatcccagaa aaccattccc agttcggatt gcaggctgca acccgcctgc atgaagccgg     1320
aatcgctagt aatcgcggat cagcatgccg cggtgaatac gttcccgggc cttgtacaca     1380
ccgcccgtca caccacgaga gtttgtaaca cccgaagtcg gtgaggtaac ctttacggag     1440
ccagccgccg aaggtggg                                                    1458

<210> SEQ ID NO 3
<211> LENGTH: 1547
<212> TYPE: DNA
<213> ORGANISM: Bacillus coagulans
<220> FEATURE:
<223> OTHER INFORMATION: B. coagulans 2-6

<400> SEQUENCE: 3
aaaggaggtg atccagccgc accttccgat acgctacct tgttacgact tcaccccaat       60
catctgtccc accttcggcg gctggctccg taaaggttac ctcaccgact tcgggtgtta     120
caaactctcg tggtgtgacg ggcggtgtgt acaaggcccg ggaacgtatt caccgcggca     180
tgctgatccg cgattactag cgattccggc ttcatgcagg cgggttgcag cctgcaatcc     240
gaactgggaa tggtttctg ggattggctt aacctcgcgg tctcgcagcc ctttgtacca     300
tccattgtag cacgtgtgta gcccaggtca taaggggcat gatgatttga cgtcatcccc     360
accttcctcc ggtttgtcac cggcagtcac cttagagtgc ccaactcaat gctggcaact     420
aaggtcaagg gttgcgctcg ttgcgggact aacccaaca tctcacgaca cgagctgacg     480
acaaccatgc accacctgtc actctgtccc ccgaagggga aggccctgtc tccagggagg     540
tcagaggatg tcaagacctg gtaaggttct tcgcgttgct tcgaattaaa ccacatgctc     600
caccgcttgt gcgggccccc gtcaattcct ttgagtttca gccttgcggc cgtactcccc     660
aggcggagtg cttaatgcgt tagctgcagc actaaagggc ggaaaccctc taacacttag     720
cactcatcgt ttacgcgtg gactaccagg gtatctaatc ctgtttgctc cccacgcttt     780
cgcgcctcag cgtcagttac agaccagaga gccgccttcg ccactggtgt tcctccacat     840
ctctacgcat ttcaccgcta cacgtggaat tccactctcc tcttctgcac tcaagcctcc     900
cagtttccaa tgaccgcttg cggttgagcc gcaagatttc acatcagact taagaagccg     960
cctgcgcgcg ctttacgccc ataattccg gacaacgctt gccacctacg tattaccgcg    1020
gctgctggca cgtagttagc cgtggctttc tggcccggta ccgtcaaggc gccgccctgt    1080
tcgaacggca cttgttcttc cccggcaaca gagttttacg acccgaaggc cttcttcact    1140
```

-continued

```
cacgcggcgt tgctccgtca gactttcgtc cattgcggaa gattccctac tgctgcctcc    1200
cgtaggagtt tgggccgtgt ctcagtccca atgtggccga tcaccctctc aggtcggcta    1260
cgcatcgttg ccttggtggg ccgttacccc gccaactagc taatgcgccg cgggcccatc    1320
tgtaagtggc agccgaagcc gcctttcctt tttcctccat gcggaggaaa aaacgatccg    1380
gtattagccc cggtttcccg cgttatccc  agtcttacag gcaggttgcc cacgtgttac    1440
tcacccgtcc gccgctaacc ttttaaaagc aagcttttaa aaggtccgca cgacttgcat    1500
gtattaggca cgccgccagc gttcgtcctg agccaggatc aaactct                 1547
```

<210> SEQ ID NO 4
<211> LENGTH: 1548
<212> TYPE: DNA
<213> ORGANISM: Bacillus coagulans
<220> FEATURE:
<223> OTHER INFORMATION: B. coagulans 36D1

<400> SEQUENCE: 4

```
agaaaggagg tgatccagcc gcaccttccg atacggctac cttgttacga cttcacccca     60
atcatctgtc ccaccttcgg cggctggctc cgtaaaggtt acctcaccga cttcgggtgt    120
tacaaactct cgtggtgtga cgggcggtgt gtacaaggcc cgggaacgta ttcaccgcgg    180
catgctgatc cgcgattact agcgattccg gcttcatgca ggcgggttgc agcctgcaat    240
ccgaactggg aatggttttc tgggattggc ttaacctcgc ggtctcgcag ccctttgtac    300
catccattgt agcacgtgtg tagcccaggt cataaggggc atgatgattt gacgtcatcc    360
ccaccttcct ccggtttgtc accggcagtc accttagagt gcccaactga atgctggcaa    420
ctaaggtcaa gggttgcgct cgttgcggga cttaacccaa catctcacga cacgagctga    480
cgacaaccat gcaccacctg tcactctgtc ccccgaaggg gaaggccctg tctccaggga    540
ggtcagagga tgtcaagacc tggtaaggtt cttcgcgttg cttcgaatta aaccacatgc    600
tccaccgctt gtgcgggccc ccgtcaattc ctttgagttt cagccttgcg gccgtactcc    660
ccaggcggag tgcttaatgc gttagctgca gcactaaagg gcggaaaccc tctaacactt    720
agcactcatc gtttacggcg tggactacca gggtatctaa tcctgtttgc tccccacgct    780
ttcgcgcctc agcgtcagtt acagaccaga gagccgcctt cgccactggt gttcctccac    840
atctctacgc atttcaccgc tacacgtgga attccactct cctcttctgc actcaagccc    900
cccagtttcc aatgaccgct tgcggttgag ccgcaagatt tcacatcaga cttaagaaac    960
cgcctgcgcg cgctttacgc ccaataattc cggacaacgc ttgccaccta cgtattaccg    1020
cggctgctgg cacgtagtta gccgtggctt tctggccggg taccgtcaag cgccgccct    1080 gttcgaacgg cacttgttct tccccggcaa cagagtttta cgaccgaag gccttcttca    1140 ctcacgcggc gttgctccgt cagactttcg tccattgcgg aagattccct actgctgcct    1200
cccgtaggag tttgggccgt gtctcagtcc caatgtggcc gatcaccctc tcaggtcggc    1260
tacgcatcgt tgccttggtg agccgttacc ccaccaacta gctaatgcgc cgcgggccca    1320
tctgtaagtg acagcaaaag ccgtctttcc ttttcctcc atgcggagga aaaaactatc    1380
cgatattagc cccggtttcc ggcgttatc  ccgatcttac aggcaggtta cccacgtgtt    1440
actcacccgt ccgccgctaa ccttttaaaa gcaagctttt aaaaggtccg cacgacttgc    1500
atgtattagg cacgccgcca gcgttcgtcc tgagccagga tcaaactc              1548
```